(12) United States Patent
Griffin et al.

(10) Patent No.: US 8,409,102 B2
(45) Date of Patent: Apr. 2, 2013

(54) MULTI-FOCUS ULTRASOUND SYSTEM AND METHOD

(75) Inventors: Weston Blaine Griffin, Niskayuna, NY (US); Douglas Glenn Wildes, Ballston Lake, NY (US); David Martin Mills, Niskayuna, NY (US); Murtuza Lokhandwalla, Clifton Park, NY (US); Christopher Robert Hazard, Niskayuna, NY (US); Warren Lee, Niskayuna, NY (US); Reinhold Bruestle, Zipf (AT)

(73) Assignee: General Electric Company, Niskayuna, NY (US)

( * ) Notice: Subject to any disclaimer, the term of this patent is extended or adjusted under 35 U.S.C. 154(b) by 400 days.

(21) Appl. No.: 12/873,026

(22) Filed: Aug. 31, 2010

(65) Prior Publication Data

US 2012/0053468 A1    Mar. 1, 2012

(51) Int. Cl.
*A61B 8/14* (2006.01)

(52) U.S. Cl. ........ 600/459; 600/407; 600/437; 600/445; 73/634

(58) Field of Classification Search .......... None
See application file for complete search history.

(56) References Cited

U.S. PATENT DOCUMENTS

| | | | | |
|---|---|---|---|---|
| 4,151,834 A | * | 5/1979 | Sato et al. | 600/446 |
| 4,756,313 A | * | 7/1988 | Terwilliger | 600/462 |
| 4,785,819 A | * | 11/1988 | Pearce | 600/446 |
| 4,806,914 A | | 2/1989 | Thomas et al. | |
| 4,807,634 A | * | 2/1989 | Enjoji et al. | 600/437 |
| 4,831,365 A | | 5/1989 | Thomas et al. | |
| 4,858,613 A | * | 8/1989 | Fry et al. | 600/439 |
| 4,918,427 A | | 4/1990 | Thomas et al. | |
| 5,088,495 A | * | 2/1992 | Miyagawa | 600/446 |
| 5,131,397 A | * | 7/1992 | Crowley | 600/463 |

(Continued)

FOREIGN PATENT DOCUMENTS

| WO | 8907909 A1 | 9/1989 |
|---|---|---|
| WO | 9324057 A1 | 12/1993 |

OTHER PUBLICATIONS

Search Report and Written Opinion from corresponding EP Application No. 11178939.2-1265 dated Dec. 23, 2011.

*Primary Examiner* — Brian Casler
*Assistant Examiner* — Serkan Akar
(74) *Attorney, Agent, or Firm* — Scott J. Asmus (57) ABSTRACT

A multi-focus probe that includes a motor communicatively coupled with a lead screw and configured to turn the lead screw about a lengthwise axis of the lead screw, wherein the lead screw includes a length having threads. The probe also includes a lead-screw nut positioned about the lead screw such that the lead-screw nut engages the threads and such that the lead-screw nut and the lead screw can move relative to one another via the threads, a transducer configured to move vertically with the lead screw, and an enclosure surrounding the transducer, wherein the enclosure includes a probe face configured to hold fluid and engage a wave emission target such that waves from the transducer can enter the target. Further, the probe includes a capture feature capable of engaging the lead-screw nut such that the lead-screw nut is vertically fixed relative to the probe face and such that the lead screw moves away from the probe face when rotating within the lead-screw nut in a first direction and moves toward the probe face when rotating within the lead-screw nut in a second direction opposite to the first direction while the lead-screw nut is engaged by the capture feature.

16 Claims, 7 Drawing Sheets

U.S. PATENT DOCUMENTS

| | | | |
|---|---|---|---|
| 5,178,150 A * | 1/1993 | Silverstein et al. | 600/463 |
| 5,187,669 A | 2/1993 | Wildes et al. | |
| 5,212,645 A | 5/1993 | Wildes et al. | |
| 5,255,681 A * | 10/1993 | Ishimura et al. | 600/437 |
| 5,497,776 A * | 3/1996 | Yamazaki et al. | 600/445 |
| 5,704,105 A | 1/1998 | Venkataramani et al. | |
| 5,730,113 A | 3/1998 | Wildes et al. | |
| 5,738,098 A | 4/1998 | Brock-Fisher et al. | |
| 5,762,066 A * | 6/1998 | Law et al. | 600/439 |
| 5,834,880 A | 11/1998 | Venkataramani et al. | |
| 5,840,032 A | 11/1998 | Hatfield et al. | |
| 5,865,163 A | 2/1999 | Wildes et al. | |
| 5,882,309 A | 3/1999 | Chiao et al. | |
| 5,897,501 A | 4/1999 | Wildes et al. | |
| 5,951,304 A | 9/1999 | Wildes et al. | |
| 6,183,419 B1 | 2/2001 | Wildes | |
| 6,198,956 B1 * | 3/2001 | Dunne | 600/407 |
| 6,559,389 B1 | 5/2003 | Kornrumpf et al. | |
| 6,822,374 B1 | 11/2004 | Smith et al. | |
| 6,831,394 B2 | 12/2004 | Baumgartner et al. | |
| 6,865,140 B2 | 3/2005 | Thomenius et al. | |
| 6,974,333 B2 | 12/2005 | Wildes et al. | |
| 7,030,536 B2 | 4/2006 | Smith et al. | |
| 7,037,746 B1 | 5/2006 | Smith et al. | |
| 7,097,619 B2 | 8/2006 | Von Behren et al. | |
| 7,105,986 B2 | 9/2006 | Wildes et al. | |
| 7,229,292 B1 | 6/2007 | Haider et al. | |
| 7,280,435 B2 | 10/2007 | Thomenius et al. | |
| 7,285,897 B2 | 10/2007 | Fisher et al. | |
| 7,293,462 B2 | 11/2007 | Lee et al. | |
| 7,299,806 B2 | 11/2007 | Lokhandwalla et al. | |
| 7,309,943 B2 * | 12/2007 | Henderson et al. | 310/323.02 |
| 7,353,056 B2 | 4/2008 | Hazard et al. | |
| 7,408,283 B2 | 8/2008 | Smith et al. | |
| 7,431,698 B2 | 10/2008 | Bruestle | |
| 7,441,321 B2 | 10/2008 | Baumgartner et al. | |
| 7,443,765 B2 | 10/2008 | Thomenius et al. | |
| 7,451,651 B2 | 11/2008 | Woychik et al. | |
| 7,491,172 B2 | 2/2009 | Bruestle | |
| 7,494,469 B2 | 2/2009 | Bruestle | |
| 7,527,592 B2 | 5/2009 | Haugen et al. | |
| 7,545,012 B2 | 6/2009 | Smith et al. | |
| 7,621,028 B2 | 11/2009 | Gelly et al. | |
| 7,622,848 B2 | 11/2009 | Lee et al. | |
| 7,694,406 B2 | 4/2010 | Wildes et al. | |
| 7,766,833 B2 | 8/2010 | Lee et al. | |
| 7,775,982 B2 | 8/2010 | Hazard et al. | |
| 2002/0128594 A1 * | 9/2002 | Das et al. | 604/67 |
| 2004/0190377 A1 | 9/2004 | Lewandowski et al. | |
| 2005/0043628 A1 | 2/2005 | Baumgartner et al. | |
| 2005/0075572 A1 | 4/2005 | Mills et al. | |
| 2005/0127793 A1 | 6/2005 | Baumgartner et al. | |
| 2006/0004290 A1 | 1/2006 | Smith et al. | |
| 2006/0058664 A1 * | 3/2006 | Barthe et al. | 600/439 |
| 2006/0116671 A1 * | 6/2006 | Slayton et al. | 606/27 |
| 2007/0066880 A1 | 3/2007 | Lee et al. | |
| 2007/0073135 A1 | 3/2007 | Lee et al. | |
| 2007/0129633 A1 | 6/2007 | Lee et al. | |
| 2007/0167802 A1 | 7/2007 | Rigby et al. | |
| 2007/0167813 A1 | 7/2007 | Lee et al. | |
| 2007/0167821 A1 * | 7/2007 | Lee et al. | 600/463 |
| 2007/0167824 A1 | 7/2007 | Lee et al. | |
| 2007/0167825 A1 | 7/2007 | Lee et al. | |
| 2007/0167826 A1 | 7/2007 | Lee et al. | |
| 2007/0180916 A1 | 8/2007 | Tian et al. | |
| 2007/0287914 A1 * | 12/2007 | Cohen | 600/443 |
| 2008/0051655 A1 | 2/2008 | Sato et al. | |
| 2008/0097403 A1 | 4/2008 | Donaldson et al. | |
| 2008/0125658 A1 | 5/2008 | Lee et al. | |
| 2008/0139893 A1 | 6/2008 | Lee et al. | |
| 2008/0139935 A1 | 6/2008 | Lin et al. | |
| 2008/0146920 A1 | 6/2008 | Lin et al. | |
| 2008/0146924 A1 | 6/2008 | Smith et al. | |
| 2008/0146937 A1 | 6/2008 | Lee et al. | |
| 2008/0200801 A1 | 8/2008 | Wildes et al. | |
| 2008/0269647 A1 | 10/2008 | Brunsveld Van Hulten | |
| 2008/0273424 A1 | 11/2008 | Wodnicki et al. | |
| 2008/0278151 A1 | 11/2008 | Wang et al. | |
| 2008/0285824 A1 | 11/2008 | Wildes et al. | |
| 2008/0287777 A1 | 11/2008 | Li et al. | |
| 2008/0287778 A1 | 11/2008 | Li et al. | |
| 2008/0287794 A1 | 11/2008 | Li et al. | |
| 2008/0287797 A1 | 11/2008 | Lee et al. | |
| 2008/0287798 A1 | 11/2008 | Lee et al. | |
| 2008/0287803 A1 | 11/2008 | Li et al. | |
| 2008/0296708 A1 | 12/2008 | Wodnicki et al. | |
| 2008/0315331 A1 | 12/2008 | Wodnicki et al. | |
| 2009/0076390 A1 | 3/2009 | Lee et al. | |
| 2009/0148967 A1 | 6/2009 | Wodnicki et al. | |
| 2009/0264767 A1 | 10/2009 | Griffin et al. | |
| 2010/0069751 A1 | 3/2010 | Hazard et al. | |
| 2010/0145310 A1 | 6/2010 | Lee et al. | |
| 2010/0191113 A1 | 7/2010 | Hazard et al. | |
| 2011/0263986 A1 * | 10/2011 | Park et al. | 600/462 |

* cited by examiner

MULTI-FOCUS ULTRASOUND SYSTEM AND METHOD

BACKGROUND OF THE INVENTION

The subject matter disclosed herein relates to ultrasound probes that may be utilized for diagnostic and/or therapeutic purposes. More particularly, present embodiments are directed to systems and methods that facilitate adjustment of a focus depth of an ultrasound probe between multiple positions while maintaining acoustic coupling.

The term ultrasound generally refers to cyclic sound pressure that has a frequency in a range that is higher than the upper limit of human hearing. A typical ultrasound frequency may include 1 to 20 megahertz. Ultrasound is frequently used for imaging purposes. For example, ultrasound is used in ultrasonography, which is a medical imaging technique that emits high frequency sound waves into a patient's body and detects echoes of the sound waves to produce images of features internal to the patient's body (e.g., blood flow images and intrauterine images). However, ultrasound may also be utilized to perform functions. For example, ultrasound may be utilized to facilitate removal of a buildup of foreign matter from a surface or for therapeutic purposes (e.g., stimulating a damaged muscle).

While there are numerous uses for ultrasound, a representative example may include a medical imaging application. In a typical ultrasound imaging application, sound waves are emitted into a patient's body from a probe and are reflected back to the probe when they hit boundaries. For example, some waves may reflect back to the probe upon reaching a boundary between fluid and tissue and other waves may reflect back to the probe upon reaching a boundary between tissue and bone. The probe detects the reflected waves and relays them to a monitor that utilizes the speed of the ultrasound and the time required to detect the reflected wave relative to the time of emission to calculate the distance from the probe to the reflecting surface. The distances and intensities of the detected waves may then be displayed to provide an image of the observed tissue. Relatively dense tissue may be distinguished from less dense tissue based on a difference in intensity because more dense tissue may reflect more ultrasound waves than less dense tissue.

Many ultrasound probes include an elevational lens that focuses ultrasound energy at a specific and fixed distance from a transducer. However, typical ultrasound images show a range of depths, and it is now recognized that since the depth at which the transducer is focused may not be consistent with a desired image, it may be desirable to adjust the depth at which the transducer is focused.

BRIEF DESCRIPTION OF THE INVENTION

In one embodiment a multi-focus probe includes a motor communicatively coupled with a lead screw and configured to turn the lead screw about a lengthwise axis of the lead screw, wherein the lead screw includes a length having threads. The probe also includes a lead-screw nut positioned about the lead screw such that the lead-screw nut engages the threads and such that the lead-screw nut and the lead screw can move relative to one another via the threads, a transducer configured to move vertically with the lead screw, and an enclosure surrounding the transducer, wherein the enclosure includes a probe face configured to hold fluid and engage a wave emission target such that waves from the transducer can enter the target. Further, the probe includes a capture feature capable of engaging the lead-screw nut such that the lead-screw nut is vertically fixed relative to the probe face and such that the lead screw moves away from the probe face when rotating within the lead-screw nut in a first direction and moves toward the probe face when rotating within the lead-screw nut in a second direction opposite to the first direction while the lead-screw nut is engaged by the capture feature.

In one embodiment, a method includes rotating a lead screw with a motor, wherein the lead screw is at least partially positioned within a probe housing including a probe face, causing a lead-screw nut to travel along threads of the lead screw based on rotation of the lead screw such that the lead-screw nut moves vertically relative to the probe face, and engaging the lead-screw nut with a capture feature such that the lead screw-nut is in a fixed position relative to the probe face and continuing to rotate the lead screw such that the lead screw moves vertically relative to the probe face into a different position thus repositioning a transducer that is coupled to an assembly that moves with the lead screw.

In one embodiment, a multi-focus probe includes a driven link coupled to a housing at a first end via hinged coupling such that the driven link is capable of rotating about the hinged coupling, a transducer link coupled with the driven link via a slot in a first end of the transducer link and a pin in a second end of the driven link, a transducer coupled to the transducer link at second end of the transducer link opposite to the first end of the transducer link, and a motor configured to rotate the driven link about the hinged coupling.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

Technical effects of the invention include providing the functionality of more than one ultrasound probe within a single unit by enabling the probe to be vertically adjusted into different positions while maintaining acoustic coupling. The varying vertical positions of the probe facilitate movement of the focus depth of the probe throughout a target (e.g., tissue) such that the functionality of multiple different probes may be achieved. Relative to conventional single probe solutions, present embodiments may provide improved image quality or treatment efficacy for both superficial and deep features by providing a multi-focus probe. With regard to diagnostic (e.g., imaging) and therapeutic (e.g., muscle stimulation) functions, present embodiments may provide flexibility in the patient population on which the probe may be utilized because the multi-focus probe may be adjusted for different focus depths corresponding to different patient types. Further, such a multi-focus functionality may facilitate tailored treatment of patients that may improve efficacy. For example, by enabling an adjustable focus depth, present embodiments may facilitate an increase in success rates in imaging applications such as catheter guidance procedures.

Present embodiments are generally directed to a system and method for adjustably focusing an ultrasound probe at different depths within a target. More particularly, the present disclosure provides systems and methods whereby the location of the focus of an ultrasound transducer can be varied in depth by mechanically shifting the position of the transducer within a probe housing. In present embodiments, the transducer may have a fixed focus, which means that the focus of emitted ultrasound is in a fixed location relative to the transducer itself, not relative to the probe housing. Accordingly, in present embodiments, the distance between the transducer and a contact surface of the probe housing (i.e., the portion of the probe that provides acoustic coupling between the probe and the target) can be changed either automatically or by a user to place the focus of the transducer in a particular region. For example, the depth of focus in a patient's tissue may be changed by moving the transducer relative to the contact surface to place the focus of the ultrasound waves in a diagnostic or therapeutic region of interest.

Figure 1:
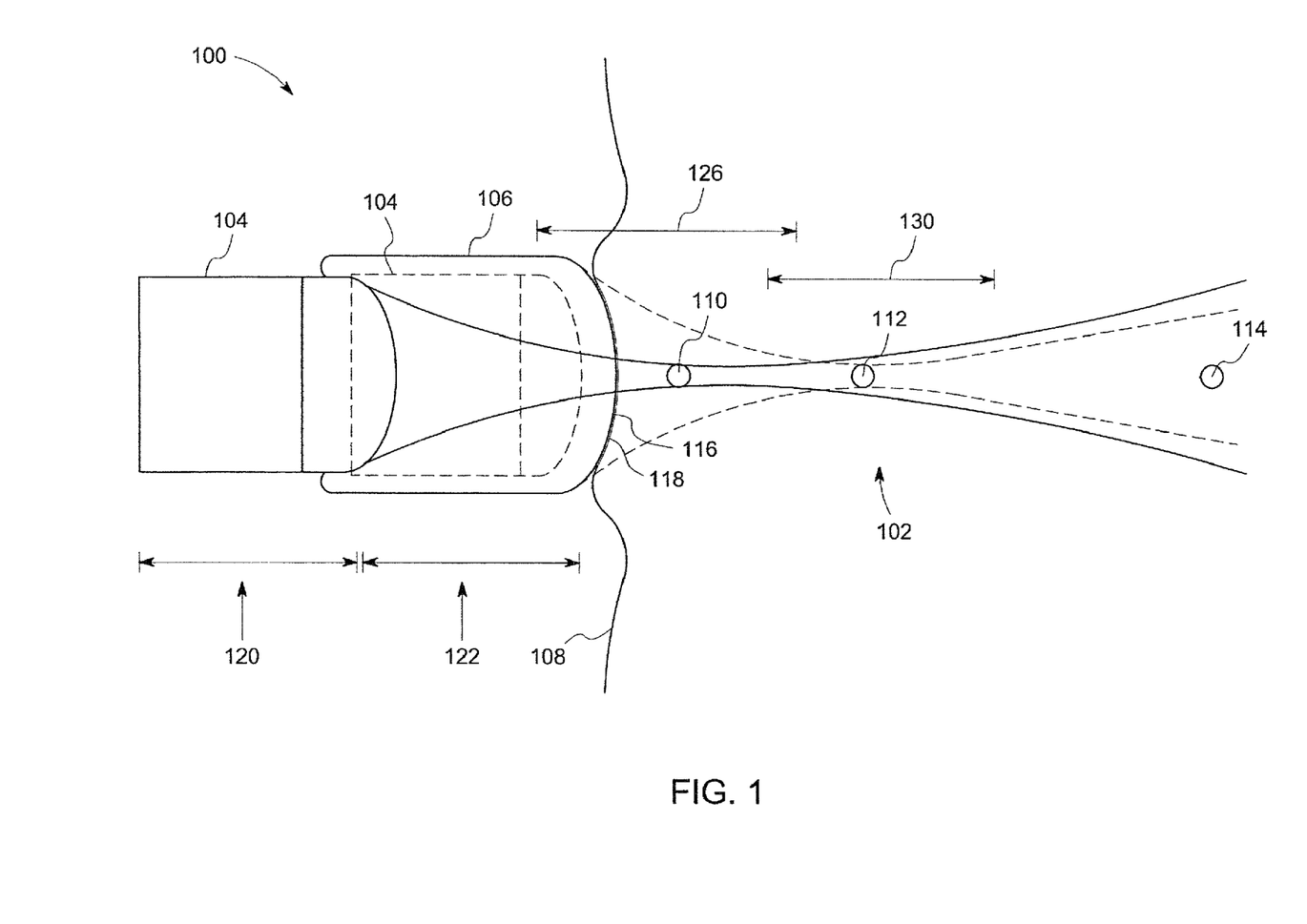
FIG. 1 is a profile view of an ultrasound probe emitting an ultrasound beam from a transducer at two different positions within a probe housing in accordance with an embodiment.

FIG. 1 illustrates a profile view of an ultrasound probe 100 emitting an ultrasound beam 102 from a transducer 104 at two different positions within a probe housing 106 in accordance with present embodiments. The ultrasound probe 100 is positioned such that a face 118 of the probe 100 is adjacent tissue 108, which includes various items of interest 110, 112, and 114. In a first position 120 of the transducer 104 relative to the probe housing 106, the transducer 104 is positioned away from a contact surface 116 between the face 118 of the probe 100 and the tissue 108. However, the probe housing 106 is filled with fluid such that acoustic coupling is maintained between the transducer 104 and the tissue in the first position 120 because the fluid fills the void provided when the transducer 104 is moved into the first position 120 from a second position 122. The fluid allows transmission of ultrasound waves between the face 118 and the transducer 104. In the second position 122, the transducer 104 is positioned near or adjacent the face 118, which is the portion of the probe housing 100 contacting the tissue 108.

The first position 120 and the second position 122 each provide different focus points within the tissue 108. Thus, each position 120, 122 provides a different optimal imaging range within the tissue 108. For example, an optimal imaging range for the first position 120 is indicated by reference numeral 126, and the optimal imaging range for the second position 122 is indicated by reference numeral 130. In view of the differing optimal imaging ranges, each position 120, 122 may provide a preferred imaging scenario for the various items of interest 110, 112, and 114. Indeed, if the fixed focus of the transducer 104 does not coincide with the region of interest, resulting image quality may suffer. However, more and better information may be provided for a region of interest if the focus depth falls within that region. For example, the first position 120 may provide a clearer and/or better defined image of the item 110 than the items 112 and 114. Similarly, the second position 122 may provide a clearer and/or better defined image of item 112 than items 110 and 114.

Figure 2:
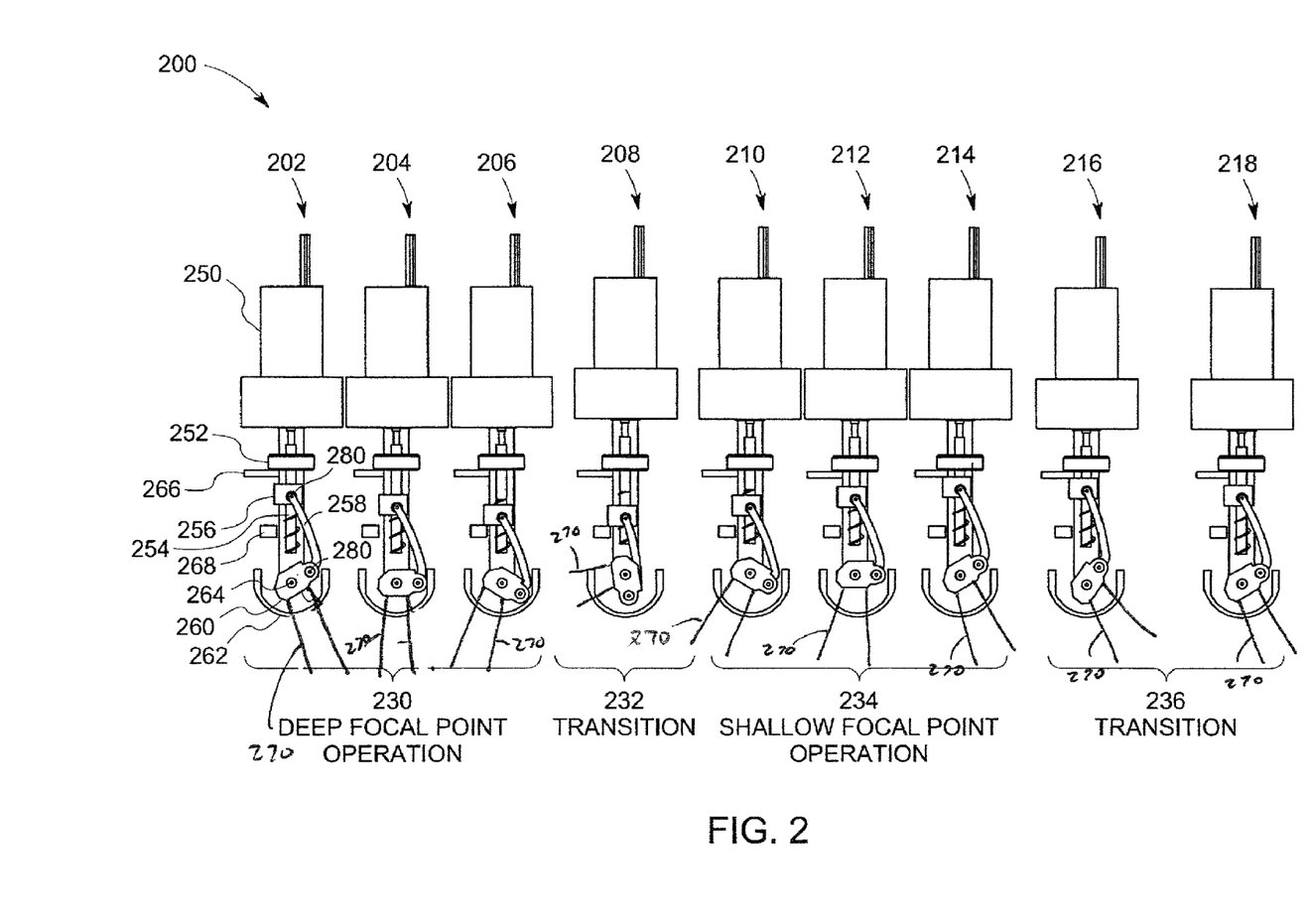
FIG. 2 illustrates a side view of an adjustable probe system in various different positions in accordance with an embodiment.

FIG. 2 illustrates a side view of an adjustable probe system 200 in various different positions in accordance with present embodiments. Specifically, the adjustable probe system 200 includes a positioning mechanism that is shown moving through positions 202, 204, 206, 208, 210, 212, 214, 216, and 218. Positions 202, 204, and 206 represent positioning of the system 200 during a deep focal point operation 230. Position 208 represents a transition from deep operation to shallow operation 232. Positions 210, 212, and 214 represent positioning of the system 200 during a shallow focal point operation 234. Positions 216 and 218 represent transition back to deep operation 236. These positions will be discussed in further detail below as they relate to the functions of the system 200 and its components.

Among other things, the system 200 includes a motor or drive mechanism 250, a fluid shaft seal 252, a lead screw 254, a lead-screw nut 256, a coupler link 258, a transducer 260 (e.g., a transducer array), a probe face 262, a pivot joint 264, an upper end stop 266, and a lower end stop 268. For instructive purposes, an ultrasound beam 270 emitted by the probe system 200 is also illustrated in the various positions of the system 200. The system 200 also includes a body (not shown). For example, the body may contain the motor 250 and/or include features that cooperate with the fluid shaft seal 252 to contain fluid about the transducer 260. In the embodiment illustrated in FIG. 2 and other embodiments, the fluid is contained in the interior portion of the probe handle so that the fluid can provide coupling between the transducer 260 and the probe face 262. While not explicitly shown in all cases, the fluid may be retained in the lower portion of the probe using a bulkhead internal to the probe. A shaft seal would be utilized around the lead screw shaft. Additionally, motor carriage/array assembly frame members extending from the motor 250 to the pivot joint 264 would also include some manner of seal, either through shaft sealing methods (contact seals) or flexible membrane seals (bag seals).

In accordance with the present disclosure, a positioning mechanism including various different mechanical features may be utilized to adjust the field of view and focus depth of the ultrasound energy provided by the ultrasound beam 270 of the transducer 260. Oscillating the transducer 260 about the pivot joint 264, as illustrated by the movement between positions 202-206 and between positions 210-214, may improve the field of view or coverage of the transducer 260. For imaging applications, oscillating the transducer enables the acquisition of a large three-dimensional field of view, without having to move the system 200 itself. In cases where oscillation of the transducer 260 is sufficiently fast (e.g., greater than approximately 7 Hz), a real-time volumetric image (4D) may be acquired and rendered. For therapy applications, oscillating the transducer enables the ultrasound therapy to be applied to a greater tissue volume without repositioning the entire system 200.

One method for achieving oscillatory motion of the transducer 260 in a compact probe handle is to use a slider-crank based drive system. The transducer 260 is equivalent to the driven link that is coupled to the slider. The slider or driving link is the lead-screw nut 256. The lead-screw nut 256 travels in a linear manner and the direction of the motion is based on the direction of rotation of the lead screw 254 that is driven by the motor 250 (e.g., a servomotor or stepper). Driving the motor 250 in a particular direction for a given time or to a given rotational position turns the lead screw 254 in the same manner. The rotation of the lead screw 254 causes the lead-screw nut 256 to advance along the lead screw 254 in a linear manner so long as the lead-screw nut 256 cannot rotate relative to the motor 250. The lead-screw nut 256 is prevented from rotating with respect to the motor 250 through pin joints 280 with the coupler link 258 that is pin jointed to the transducer 260 which is pin jointed to the body (e.g., motor frame/carriage housing). It should be noted that pin joints are indicated by reference numeral 280 and the pin joints 280 have parallel axes in the illustrated embodiment. The pins joints 280 are also parallel to the pivot joint 264. The pin joints 280 function as hinges such that they hingedly couple the indicated features. The linear motion of the lead-screw nut 256 is transmitted to the transducer 260 through the coupler link 258, which is coupled to the transducer 260 at a position that is not at the transducer's rotational axis. The linear motion of the lead-screw nut 256 thus imparts a rotational motion of the transducer 260 about the axis-of-rotation of the transducer 260. Thus, an oscillatory motion of the motor output also causes a rotational oscillatory motion of the transducer 260, as represented by positions 202, 204, and 206, for example.

The system 200 provides both 4D motion and the capability to change focus using only one actuator to achieve both actions. Indeed, in accordance with present embodiments, the system 200 may utilize the slider-crank mechanism to create the 4D motion oscillation of the transducer 260, as discussed above. Further, the system may achieve focus change by repositioning the transducer 260 with respect to the probe face 262 (e.g., linearly moving the pivot joint 264 relative to the probe face 262). This may be achieved by driving the lead-screw nut 256 against the lower end-stop 268, which is a capture feature fixed relative to the probe (e.g., coupled to the housing via a pivot joint). With the lead-screw nut 256 abutting the lower end-stop 268, the motor 250 continues driving the lead screw 254 in the same rotational direction. A motor carriage and frame members attached to the transducer 260 are able to slide relative to the probe housing 260, as represented by the movement of the motor 250 illustrated between positions 206 and 208, for example. The driving action of the lead screw 254 then causes the motor carriage (e.g., motor 250) and the transducer 260 to move away from the probe face 262, transitioning (as represented by position 208) from deep focal point operation 230 to shallow focal point operation 234. During this transition, the transducer rotates to an extreme position. With the carriage in its new position relative to the probe face 262, the motor 250 can then drive the lead screw 254 to oscillate the transducer 260 and achieve 4D motion, as represented by positions 210-214. To return to the starting position 202, the lead screw 254 over-drives the lead-screw nut 256 against the upper end-stop 266, and in a similar manner causes the motor carriage (e.g., motor 250) to move closer to the probe face 262 such that the transducer 260 returns to the deep focal point operation 230. In accordance with present embodiments, no additional actuation other than the single motor 250 (or stepper) may be needed to achieve this 4D motion and focus change capability. To maximize the overdrive range-of-motion (i.e., the distance between the deep focal point operation position 230 and the shallow focal point operation position 234), the curved or bent coupler link 258 can be used. Also, it should be noted that it may be beneficial to utilize friction detents (or magnets) at the extreme positions to hold the motor-carriage/array assembly in place.

Figure 3:
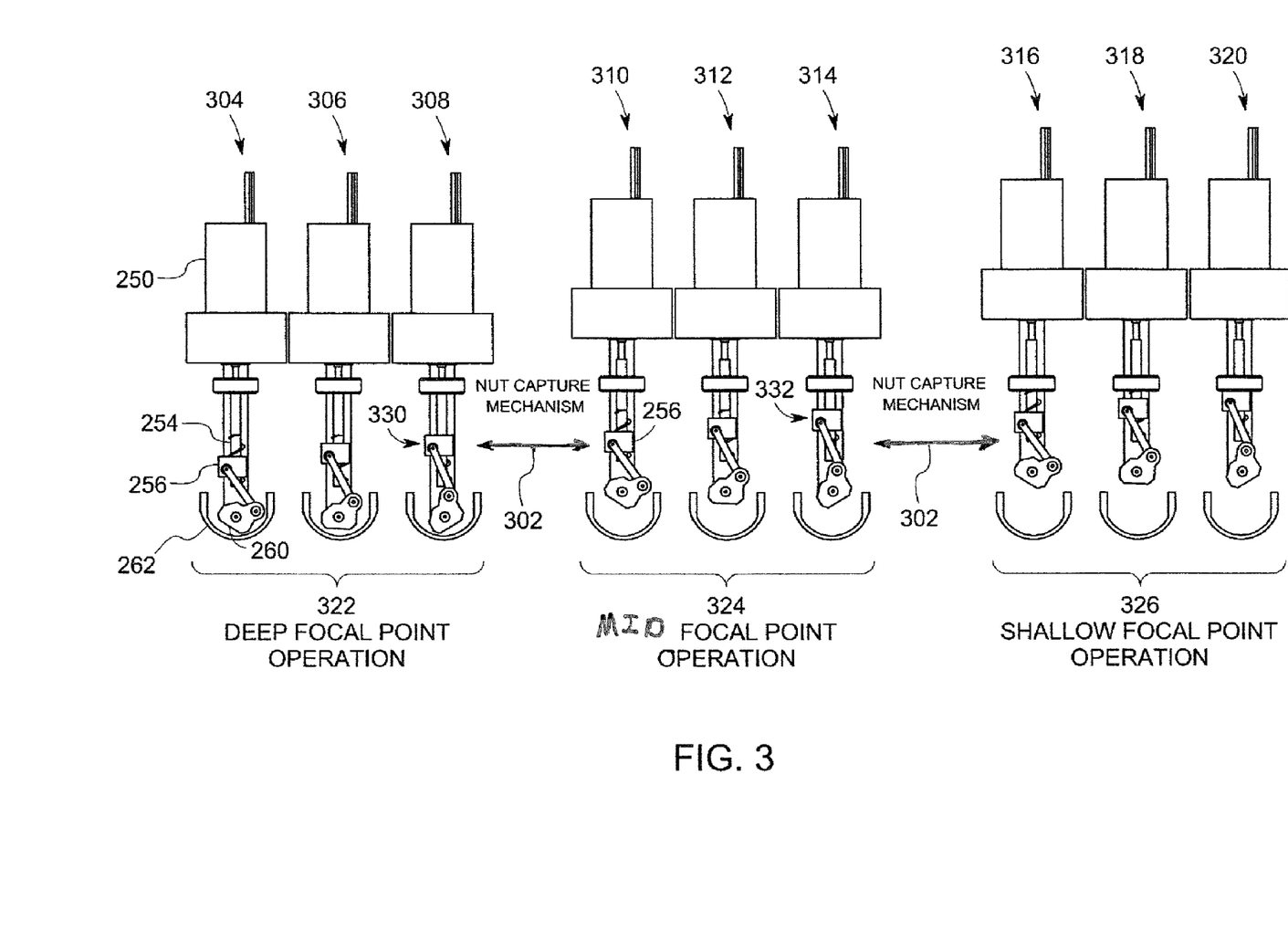
FIG. 3 illustrates a side view of an adjustable probe system in various different positions, wherein a nut capture feature is utilized in accordance with an embodiment.

FIG. 3 illustrates a side view of an adjustable probe system 300 in various different positions, wherein a nut capture feature 302 is utilized in accordance with present embodiments. Specifically, the adjustable probe system 300, which includes features similar to those of probe system 200, is shown moving through positions 304, 306, 308, 310, 312, 314, 316, 318, and 320. Positions 304, 306, and 308 represent positioning of the system 300 during a deep focal point operation 322. Positions 310, 312, and 314 represent positioning of the system 300 during mid-depth focal point operation 324. Positions 316, 318, and 320 represent positioning of the system 300 during a shallow focal point operation 326. Transitions between the operation depths are facilitated by the nut capture mechanism 302. In some embodiments, the nut capture mechanism 302 includes two separate actuators positioned at different locations 330 and 332. In other embodiments, the nut capture mechanism 302 may include a single actuator that cooperates to provide resistance at both locations 330 and 332. For example, the same actuation may cause different peg components to engage a hole or receptacle in the lead-screw nut 256 depending on the position of the lead-screw nut 256.

The system 300 provides both 4D motion and focus change capability using only a motor 250 and two actuators to achieve both actions. The 4D motion oscillation of the transducer may be achieved through the slider-crank mechanism as discussed above with regard to FIG. 2. Focus change is achieved by driving the lead-screw nut 256 to a specific position and engaging the nut capture feature 302 that captures the lead-screw nut 256 and holds it fixed relative to the probe housing. With the lead-screw nut 256 captured, the motor 250 continues driving the lead screw 254 in the same rotational direction. Thus, the motor carriage and frame members attached to the transducer 260 slide relative to the probe housing. The driving action of the lead screw 254 then causes the motor carriage and transducer 260 to move away from the probe face 262, transitioning from deep focal point operation 322 to a shallower or mid-depth focal point operation 324. During the transition motion, the transducer rotates within the normal range-of-motion. At this point, the nut capture mechanism 302 releases the lead-screw nut 256 to allow for normal 4D operation. The nut capture mechanism 302 may also simultaneously engage the motor-carriage/array assembly to prevent any relative motion with the probe housing. As shown in FIG. 3, with a nut-capture system 302 in multiple locations, such as location 330 and location 332, it is possible to increase the distance between the deep-focal point 322 and the shallow-focal point 326 and have intermediate operational points, such as the mid-depth focal point operational point 324. To return to the deep focal point operation position 322, such that the transducer is at its closest operating point relative to the probe face 262, the procedure discussed above with regard to system 300 may be reversed. Again, it may be beneficial to utilize friction detents (or magnets) at the extreme and intermediate positions to hold the motor-carriage/array assembly in place. Alternatively, it may be possible to utilize the same actuator that engages the nut in one state to engage the motor-carriage/array assembly in the other state. In such an embodiment, the actuator would be fixed relative to the probe housing and the probe face 262.

Figure 4:
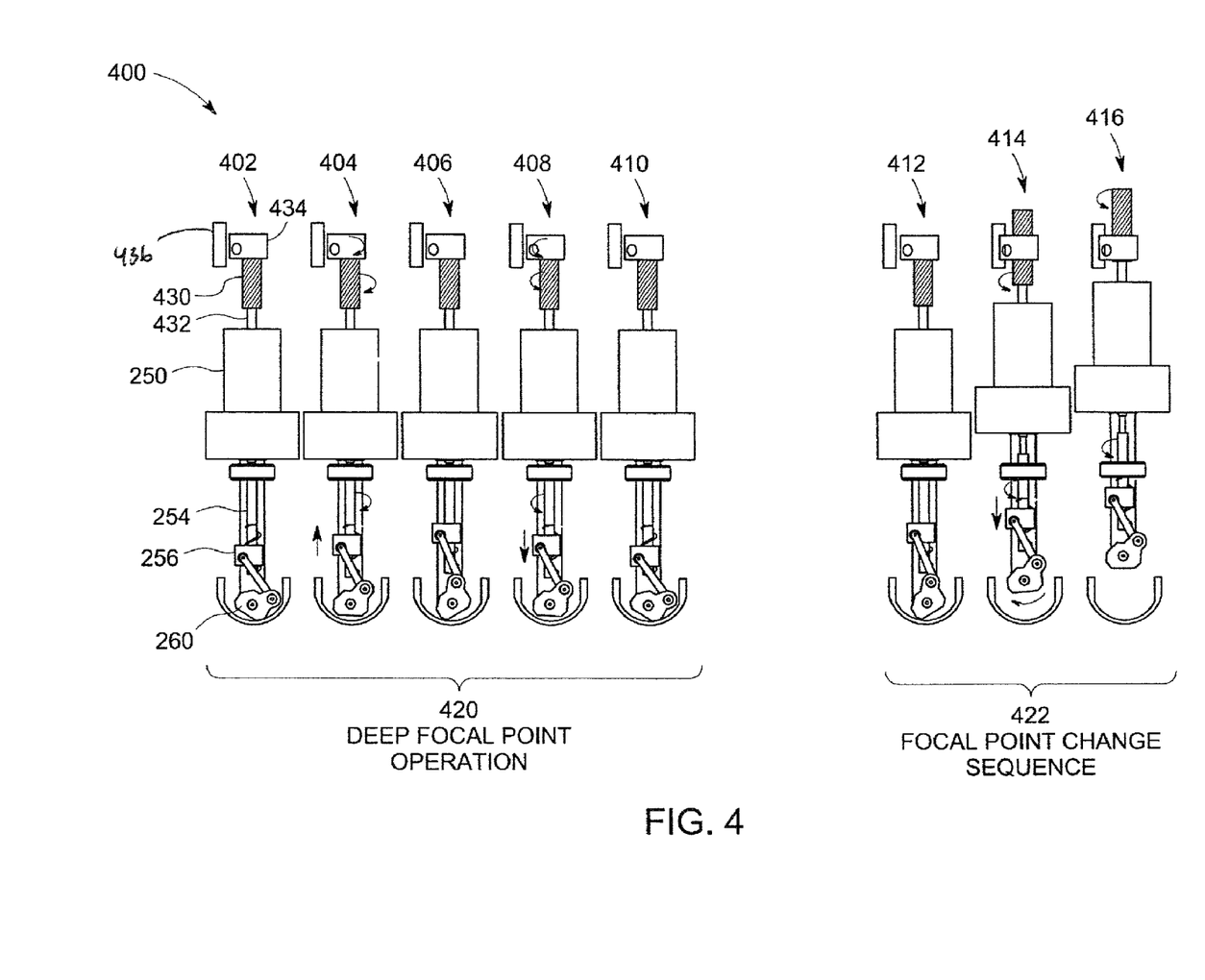
FIG. 4 illustrates a side view of an adjustable probe system in various different positions, wherein a dual lead screw feature is utilized in accordance with an embodiment.

FIG. 4 illustrates a side view of an adjustable probe system 400 in various different positions, wherein a dual lead screw feature is utilized in accordance with present embodiments. Specifically, the adjustable probe system 400, which includes features similar to those of probe system 200, is shown moving through positions 402, 404, 406, 408, 410, 412, 414, and 416. Positions 402, 404, 406, 408, and 410 represent positioning of the system 400 during a deep focal point operation 420. Positions 412, 414, and 416 represent transitional operation 422.

In the embodiment illustrated by FIG. 4, the motor 250 has an additional lead screw, which may be referred to as an upper lead screw 430. The upper lead screw 430 is positioned on a back or upper shaft 432, with a smaller lead than the lead screw 254. The upper lead screw 430 also has a lead-screw nut, which may be referred to as the upper lead-screw nut 434. During normal 4D motions, the upper lead-screw nut 434 spins freely with the upper lead-screw 430. It should be noted that the upper lead-screw nut 434 has some friction torque to avoid inertial driving of the lead screw 430. The motor carriage and frame members attached to the transducer 260 are able to slide relative to the probe housing. The focus change is achieved by first driving the main slider-crank (lower) lead-screw nut 254 to a position that is closest to the motor 250, which results in an extreme rotational position of the transducer 260. A nut engaging mechanism 436 then engages and fixes the upper lead-screw nut 434 to stop it from spinning. This also fixes the lead-screw nut 434 relative to the probe housing and/or probe face 262. As the motor 250 drives in the opposite direction, both lead screws 430 and 254 rotate. As the upper lead screw 430 rotates with the upper lead-screw nut 434 fixed, the motor 250 effectively pulls the motor-carriage and transducer 260 away from the probe face 262, moving the transducer 260 from a deep focal point operation position 420 to a shallow focal point operation position 416. Simultaneously, the lower lead screw 254 is also rotating, thus causing the lower lead-screw nut 256 to move linearly towards a rotation point, and thus causing the transducer 260 to rotate from its location in position 412 to that in position 416. The final orientation of the transducer 260 and the focus change height will depend on the ratio of the lead screw pitches. For example, with a lower lead of 3.18 mm and an upper lead of 12.7 mm (a lead screw ratio of 4), the transducer 260 will move through a 30 degree motion for a 10 mm focal change. In some embodiments, more vertical motion may be achieved by moving through a higher range of degrees (e.g., 60 degrees of motion).

Figure 5:
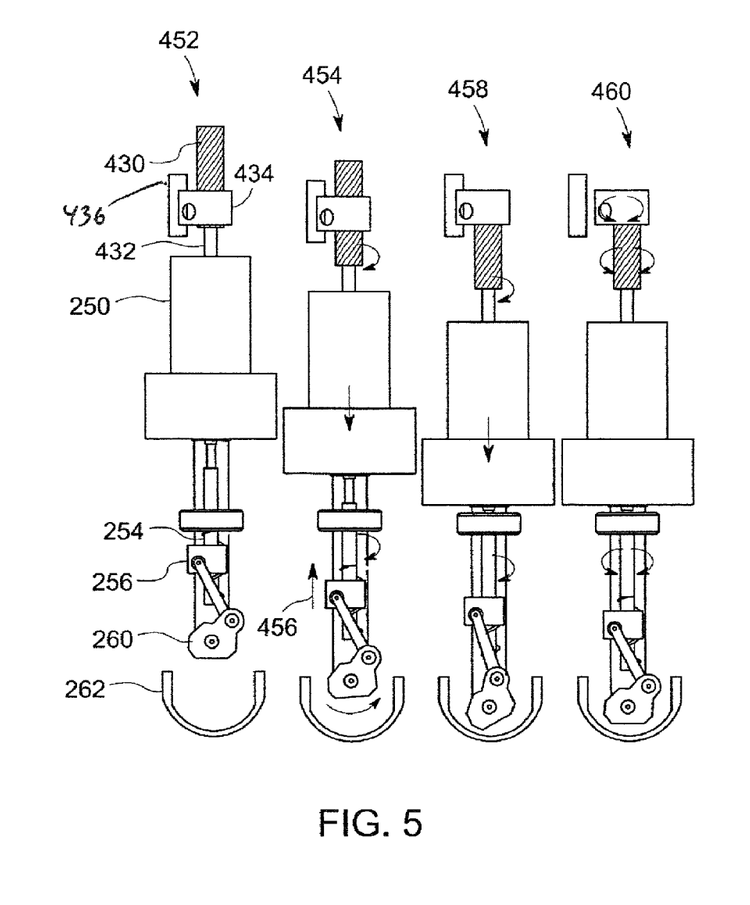
FIG. 5 illustrates the steps of moving the system of FIG. 4 from a shallow focal point operation position to a deep focal point operation position with dual lead screws in accordance with an embodiment.

FIG. 5 illustrates the steps of moving the system 400 of FIG. 4 from a shallow focal point operation position 416 back to the deep focal point operation position 420 with the dual lead screws 430 and 254. The process is similar to that described above with respect to FIG. 4, but the motor 250 rotates in the opposite direction. Specifically, as illustrated by position 452, the transducer 260 is positioned in the previous final position near a lowest relative position of the driving nut 434. Next, as illustrated by position 454, the upper nut engaging mechanism 436 is engaged to prevent the upper nut 434 from spinning. As the motor 250 and lead-screw nut 256 move upwards relative to lead-screw 254 (as illustrated by arrow 456), the transducer 260 will tend to rotate counter clockwise, as represented by position 458. The final orientation of the transducer 260 and the final vertical position of the motor 250 and transducer 260, as illustrated by position 460, should match initial position of the prior change sequence illustrated in FIG. 4.

Figure 6:
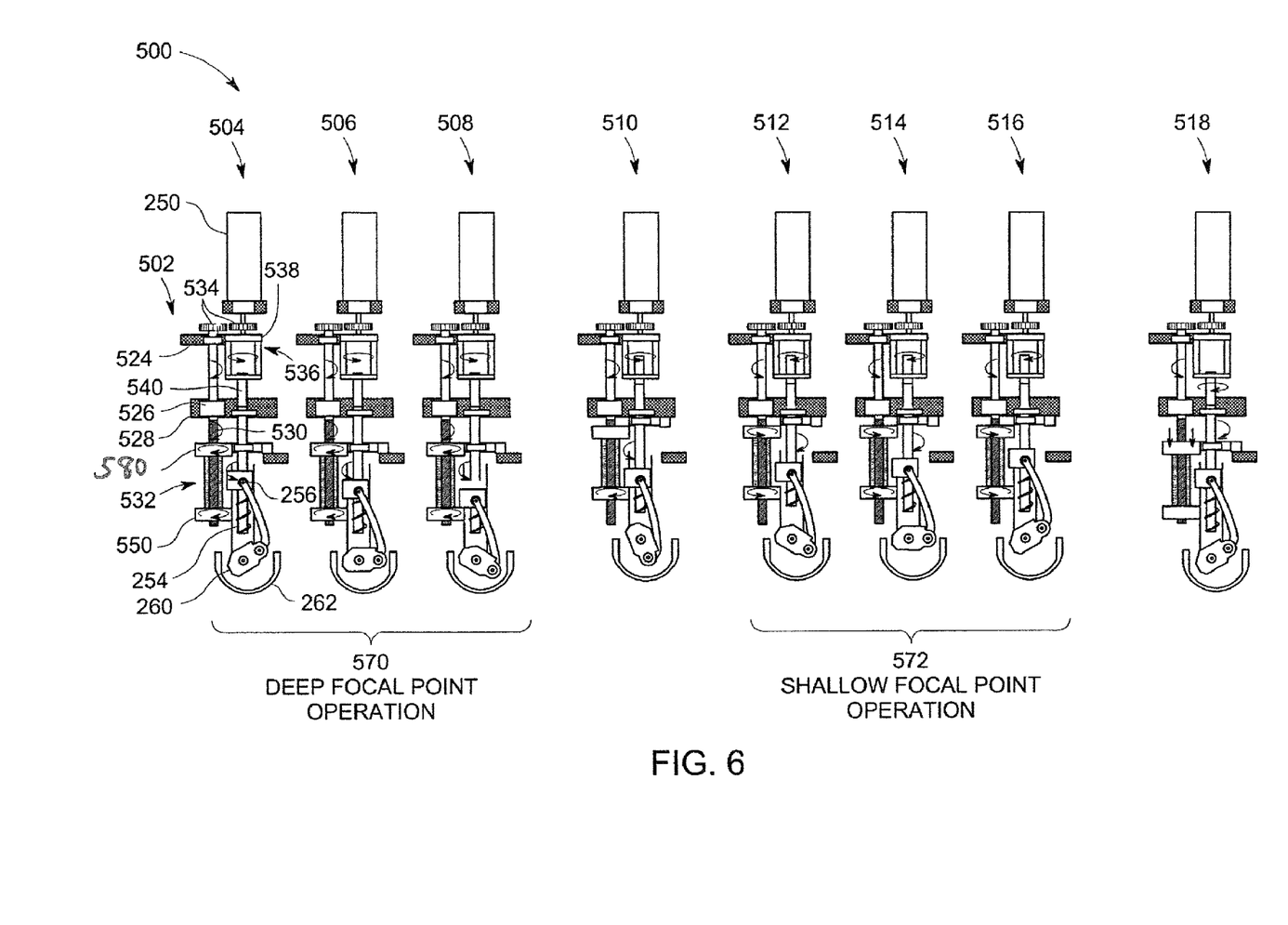
FIG. 6 illustrates a side view of an adjustable probe system in various different positions, wherein an elevator subsystem is utilized to provide additional vertical movement in accordance with an embodiment.

FIG. 6 illustrates a side view of an adjustable probe system 500 in various different positions, wherein an elevator subsystem 502 is utilized to provide additional vertical movement. Specifically, FIG. 6 illustrates the probe system 500 in positions 504, 506, 508, 510, 512, 514, 516, and 518.

The system 500 includes components similar to those of the previously described embodiments, which are designated with like reference numerals. The system 500 also includes various additional components. For example, the system 500 includes an elevator subsystem 502, which includes a thrust bearing 524, a fluid seal 526 positioned within a fluid bulk head 528, an elevator lead screw 530, and an elevator nut assembly 532. The elevator subsystem 502 functions to rotate the elevator lead screw 530 in an opposite direction compared to the main lead screw 254 based on the interaction between spur gears 534, which are mechanically engaged and respectively coupled to the elevator lead screw 530 and the main lead screw 254. The motor 250 couples to the main lead screw 254 via a spline drive 536, which includes a spline housing 538 and a spline 540. The spline drive 536 enables vertical movement of the lead screw 256 relative to the body by facilitating movement of the spline 540 in and out of the spline housing 538.

In operation, the elevator nut assembly 532 rotates in an opposite direction compared to the lead-screw nut 256. The elevator nut assembly 532 is normally freely rotating due to drag torque and thus does not change linear position with rotation of the elevator lead screw 530. However, when the lead-screw nut 256 is driven into a lower elevator nut 550 of the elevator nut assembly 532, the counter rotating screws and nut traveling in different directions keep the lead-screw nut 256 and the lower elevator nut 550 pressed against each other. Thus, the elevator nut assembly 532 cannot freely rotate and it moves vertically based on the rotation of the elevator lead screw 530, as represented by position 510. The motion of the elevator nut assembly 532 is used to reposition the transducer assembly from a deep focus operation point 570 to a shallow focus operational point 572 and vise-versa. During this transition, the transducer 260 rotates to an extreme position. As indicated above, the spline 540 can move into and out of the spline housing 538 to accommodate such vertical position changes. Indeed, in the illustrated embodiment of FIG. 6, the motor 250 does not move because the spline drive 536 is used to couple the output shaft of the motor 250 to the main lead screw 254. Again, it may be desirable to utilize friction detents (or magnets) at the extreme and intermediate positions to hold the motor-carriage/array assembly in place. This method enables a larger focus position change as compared to the overdrive method alone.

In order to return the system to the deep focus point position 570, the lead-screw nut 256 is driven against an upper elevator nut 580 of the elevator nut assembly 532. As was the case when the lower elevator nut 550 was pressed against the lead-screw nut 256, the elevator assembly 532 can no longer freely rotate and thus it moves vertically based on the rotation of the elevator lead screw 530, which is now rotating in a different direction, as generally depicted with regard to the position 518. As a result, the elevator nut assembly 532 begins transitioning the transducer 260 from the shallow focus operation point 572 back to the deep focus operation point 570.

Figure 7:
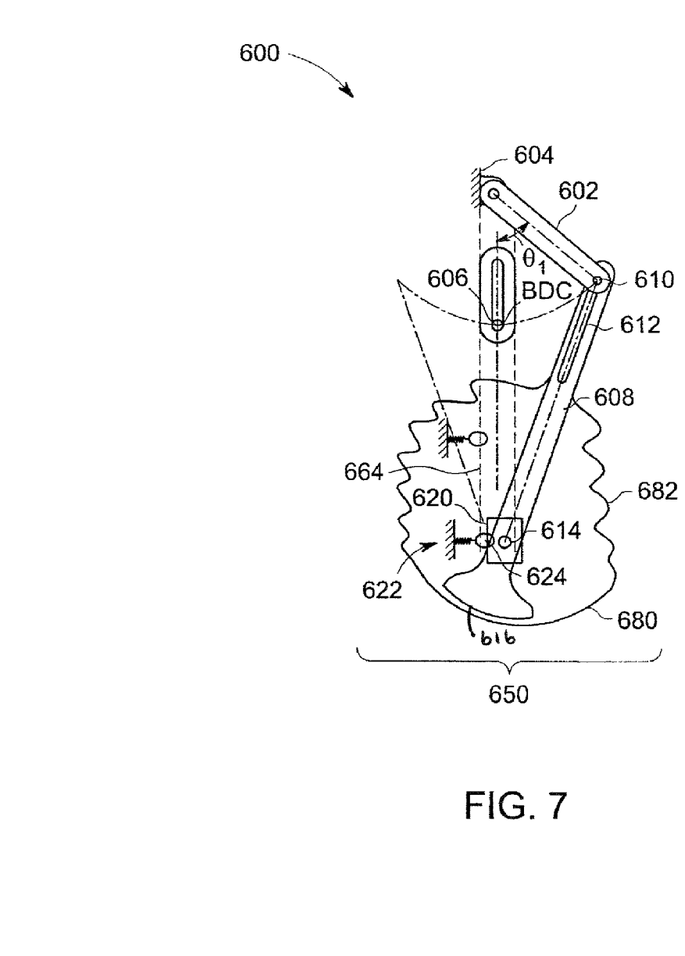
FIGS. 7 and 8 illustrate an adjustable probe assembly that is capable of providing both 4D motion and focus change capability using a crank-rocker slotted system in accordance with an embodiment.

FIG. 7 illustrates an adjustable probe assembly 600 that is capable of providing both 4D motion and focus change capability using a crank-rocker slotted system in accordance with present embodiments. In this embodiment, an input link 602 is driven in an oscillatory motion by a motor 604 such that it is oscillating about a bottom-dead-center point 606 (e.g., +/−45°). The motion is transferred from the input link 602 to a transducer link 608 via a pin 610 and slot 612. The transducer link 608 thus oscillates about a bottom axis 614 and a transducer 616, which is fixed to the transducer link 608, likewise oscillates. The transducer link 608 is disengagably held in position at the bottom axis 614 via a block 620 that is held in place with a spring detent 622 attached to a fixed part of the system (e.g., a wall) and that passes into an opening 624 in the block 620.

Figure 8:
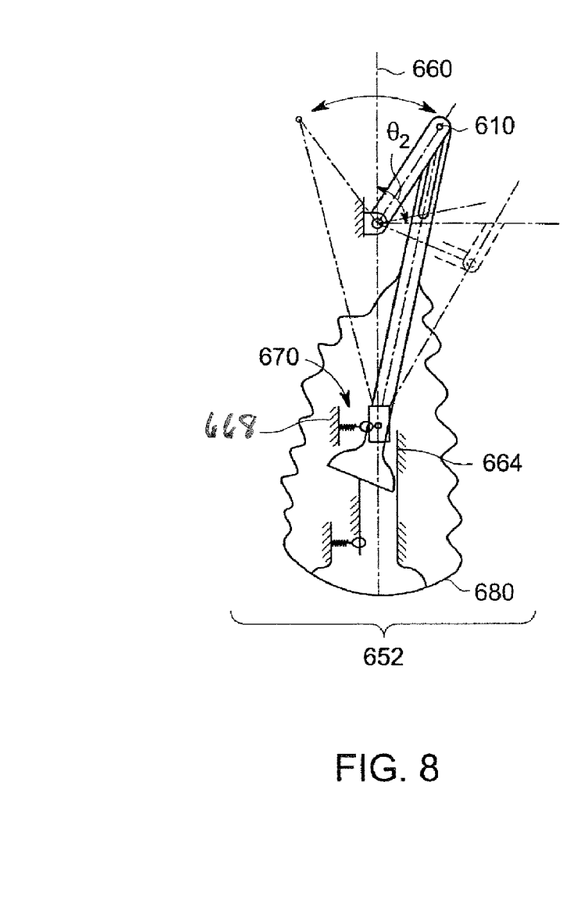

The focus position of the transducer 616 can be changed from a deep-focal point operation 650 to a shallow-focal point operation 652 by overdriving the input link 602 towards a top-dead-center position 660, as illustrated by FIG. 8. Assuming a sufficient torque margin, the driving pin 610 reaches a top end of the slot 612 on the transducer link 608 and continues to drive the transducer link 608. This in turn causes the block 620 to decouple from the spring detent 622. As the driven link 602 continues towards the top-dead-center point 660, the block 620 is guided vertically along a vertical slot 664 towards a top axis point 668, which has a second spring detent 670. The spring detent 670 cooperates with the block 620 to fix the axis point at a new height. The slot 664 and detents 622, 670 are fixed relative to the probe housing and a probe face 680. The driving link 602 can then oscillate about the top-dead-center position 660 for normal 4D motion of the transducer 616, with the transducer 616 in the shallow focus position 652. To change the position back to the deep focus position 650, the driven link 602 is overdriven in the opposite direction, towards the bottom-dead-center point 606.

It should be noted that, as with the previously described embodiments, fluid may be used to facilitate transmission of waves from the transducer through the probe face 680. In the illustrated embodiment, a sealing bag 682 is attached to the slotted link 608. The sealing bag 682 surrounds the transducer 616 in the two positions illustrated by FIGS. 7 and 8 for proper fluid coupling of the transducer 616 to the probe face 680. The sealing bag 682 may be fixed to the probe face 680 and the slotted link 602 to allow for variable fluid standoff for acoustic coupling.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A multi-focus ultrasound probe, comprising:
an enclosure surrounding an ultrasound transducer, wherein the enclosure includes a probe face configured to engage a wave emission target such that waves from the transducer can enter the target via the face;
a positioning mechanism configured to oscillate the transducer about an axis and configured to adjust a focal point operation depth of the transducer by moving the transducer towards or away from the probe face;
a fluid contained within the enclosure, wherein the fluid fills space between the transducer and the probe face;
comprising a drive mechanism configured to drive a slider along a linear component of the positioning mechanism such that a link coupled to a side of the transducer causes the transducer to pivot about the axis of the transducer;
wherein the slider is a lead-screw nut coupled to a lead screw such that the lead-screw nut engages threads of the lead screw and rotation of the lead screw when the lead-screw nut is not rotating moves the lead-screw nut along a length of the lead screw via the threads;
comprising a capture feature capable of engaging the lead-screw nut such that the lead-screw nut is vertically fixed relative to the probe face and such that the axis moves away from the probe face when the lead screw is rotating in a first direction and toward the probe face when the lead screw is rotating in a second direction opposite the first direction while the lead-screw nut is engaged by the capture feature;
wherein the positioning mechanism comprises;
a driven link capable of rotating about a hinged coupling at a first end of the driven link;
a transducer link coupled with the driven link via a slot in a first end of the transducer link and a in in a second end of the driven link, wherein a second end of the transducer link is coupled to the transducer; and
a motor configured to rotate the driven link about the hinged coupling.

2. The multi-focus ultrasound probe of claim 1, wherein the positioning mechanism is configured to move the axis linearly toward or away from the probe housing.

3. The multi-focus ultrasound probe of claim 1, wherein a drive mechanism is communicatively coupled with the positioning mechanism to drive the transducer towards or away from the probe face.

4. The multi-focus ultrasound probe of claim 3, wherein the drive mechanism is configured to drive the positioning mechanism to oscillate the transducer about the axis.

5. The multi-focus ultrasound probe of claim 1, wherein the lead-screw nut comprises a receptacle and the capture feature comprises an actuator configured to engage the receptacle.

6. The multi-focus ultrasound probe of claim 1, wherein the capture feature comprises a pair of pegs located in different positions along a length of the lead screw.

7. The multi-focus ultrasound probe of claim 1, wherein the positioning mechanism comprises a first lead screw and a second lead screw communicatively coupled with a dual-shaft motor, a first lead-screw nut engaged with the first lead screw such that the lead-screw nut engages threads of the first lead screw and rotation of the first lead screw when the lead-screw nut is not rotating moves the lead-screw nut along a length of the first lead screw via the threads, and a second lead-screw is engaged with the second lead screw such that the second lead-screw nut is capable of free spinning with the second lead screw unless engaged by a secondary capture feature coupled to the enclosure.

8. A multi-focus ultrasound probe, comprising:
a motor communicatively coupled with a lead screw and configured to turn the lead screw about a lengthwise axis of the lead screw, wherein the lead screw includes a length having threads;
a lead-screw nut positioned about the lead screw such that the lead-screw nut engages the threads and such that the lead-screw nut and the lead screw can move relative to one another via the threads;

an ultrasound transducer configured to move vertically with the lead screw;

an enclosure surrounding the transducer, wherein the enclosure includes a probe face configured to hold fluid and engage a wave emission target such that waves from the transducer can enter the target;

a capture feature capable of engaging the lead-screw nut such that the lead-screw nut is vertically fixed relative to the probe face and such that the lead screw moves away from the probe face when rotating within the lead-screw nut in a first direction and moves toward the probe face when rotating within the lead-screw nut in a second direction opposite to the first direction while the lead-screw nut is engaged by the capture feature; and a coupler link that hingedly attaches to the lead-screw nut and hingedly attaches to the transducer to provide a coupling between the transducer and the lead-screw nut.

9. The multi-focus ultrasound probe of claim 8, wherein the capture feature includes a first end stop coupled to the enclosure between the motor and the lead-screw nut such that the lead-screw nut engages the first end stop when the lead-screw nut passes along the lead screw a first distance toward the motor, and a second end stop coupled to the enclosure between the probe face and the lead-screw nut such that the lead-screw nut engages the second end stop when the lead-screw nut passes along the lead screw a second distance toward the probe face.

10. The multi-focus ultrasound probe of claim 8, wherein the motor comprises a dual-shaft motor and the dual-shaft motor communicatively couples with a secondary lead screw on a side of the dual-shaft motor opposite the lead screw.

11. The multi-focus ultrasound probe of claim 10, wherein the secondary lead screw is coupled to a secondary lead-screw nut capable of free spinning with the secondary lead screw unless engaged by a secondary capture feature coupled to the enclosure.

12. The multi-focus ultrasound probe of claim 8, wherein the capture feature includes an elevator nut assembly configured to move relative to the probe face based on mechanical coupling of an elevator subassembly to the motor.

13. A method, comprising:

rotating a lead screw with a motor, said motor turning the lead screw about a lengthwise axis of the lead screw, wherein the lead screw is at least partially positioned within an ultrasound probe housing including a probe face;

causing a lead-screw nut to travel along threads of the lead screw based on rotation of the lead screw such that the lead-screw nut moves vertically relative to the probe face;

engaging the lead-screw nut with a capture feature such that the lead screw-nut is in a fixed position relative to the probe face and continuing to rotate the lead screw such that the lead screw moves vertically relative to the probe face into a different position thus repositioning an ultrasound transducer that is coupled to an assembly that moves with the lead screw;

surrounding the transducer with an enclosure, wherein the enclosure includes a probe face holding fluid and engaging a wave emission target such that waves from the transducer enter the target;

providing a capture feature engaging the lead-screw nut such that the lead-screw nut is vertically fixed relative to the probe face and such that the lead screw moves away from the probe face when rotating within the lead-screw nut in a first direction and moves toward the probe face when rotating within the lead-screw nut in a second direction opposite to the first direction while the lead-screw nut is engaged by the capture feature; and hingedly attaching a coupler link between the lead-screw nut and the transducer to provide a coupling between the transducer and the lead-screw nut.

14. The method of claim 13, wherein engaging the lead-screw nut with a capture feature comprises pressing an end of the lead-screw nut against a fixed end stop or an actuator that is coupled with the ultrasound probe.

15. The method of claim 13, wherein engaging the lead-screw nut with a capture feature comprises pressing an end of the lead-screw nut against an elevator nut traveling in an opposite direction relative to the movement of the lead-screw nut along the lead screw.

16. The method of claim 13, comprising rotating a secondary lead screw that is coupled with a normally free spinning secondary nut with the motor on a side of the motor opposite to the lead screw.

* * * * *